US00PP08532P

United States Patent [19]

Bridges

[11] Patent Number: Plant 8,532

[45] Date of Patent: Jan. 11, 1994

[54] MINIATURE ROSE PLANT NAMED 'BRIFIRE'

[76] Inventor: Dennis A. Bridges, 2734 Toney Rd., Lawndale, N.C. 28090

[21] Appl. No.: 831,192

[22] Filed: Jan. 31, 1992

[51] Int. Cl.[5] ..... A01H 5/00
[52] U.S. Cl. ..... Plt./7.1
[58] Field of Search ..... Plt. 7.1, 11, 12, 22

*Primary Examiner*—Howard J. Locker
*Assistant Examiner*—E. F. McElwain

[57] ABSTRACT

A new and distinct variety of miniature rose plant characterized by a profusion of exhibition form blooms that are an unusual combination of colors, consisting of yellow, pink, and vibrant red, with a strong fruity fragrance, held on long stems on a strong plant.

1 Drawing Sheet

BACKGROUND OF THE INVENTION

1. Field of the Invention

The present invention relates to a new and distinct variety of miniature rose plant which has been given the international variety recognition designation "Brifire", and is to be marketed in this country under the synonym "Gabriel's Fire".

2. Plants Related to the Invention

The plant of this invention was originated as a result of a planned breeding program which had as a seed partent "Sachet" (U.S. Plant Pat. No. 5,967) also of the miniature rose class. While the pollen parent of "Brifire" is not known with certitude, it was one of a number of selected miniature varieties from which pollen had been taken for crossing with "Sachet", in the hope of attaining a new plant having some of the better traits of the seed parent and any one of the pollen parent plants involved in the program. The plant of this disclosure is a selection from the progeny of the stated cross(es), and has been asexually reproduced by the taking and rooting of stem cuttings, as performed at Lawndale, N.C., and shows that the foregoing characteristics and distinctions come true to form and are established and transmitted through succeeding propagations, establishing "Brifire" is stable.

SUMMARY OF THE INVENTION

Among the new and novel characteristics which are possessed by this plant, singly and in combination, which distinguish it from its parents and all other plants of which I am aware are:

1. Blooms of unusual red and yellow blend coloration that are well formed and blemish resistant. Showing exceptional form and substance.

2. Abundant blooms borne singly, and in clusters of up to 5 blooms, on long strong stems.

3. An unusually strong, fruity fragrance.

4. An abundance of semi-glossy, medium to dark green foliage which pleasingly contrasts with and highlights the blooms of a combination of yellow and pink to vibrant red shades.

5. Higher than usual disease resistance to common rose diseases with a higher than usual level of vigor, and growing to a height which is typical of roses of this market class to produce a plant which attractively appoints the home garden while providing cut flowers of exhibition form and quality.

BRIEF DESCRIPTION OF THE DRAWING

The single sheet of the accompanying drawing is a photograph which shows typical specimens of the flowers of the new variety in different stages of development as well as the coloration thereof as accurately as possible in color illustrations of this type.

BOTANICAL DESCRIPTION

The following is a detailed botanical description of my new variety of miniature rose. With color terminology in accordance with *The Royal Horticultural Society Colour Chart* (R.H.S.C.C.), except where common dictionary terms of color definition are employed.

Type: Hardy dwarf, bushy, compact, seedling, greenhouse, outdoors, cut flower, garden decoration, potted plant.

Commercial class: Miniature.

International recognition Name: "Brifire".

Commercial synonym: "Gabriel's Fire".

Observations were made from specimens gown outdoors at Cleveland County, N.C., USA, in June, 1991.

Type: Miniature Rose.

Blooming Habit: Continuous.

Bud:

*Size.*—Large.

*Length.*—1¾ cm Just before opening.

*Form.*—Pear shaped.

*Color.*—When sepals first divide — Yellow, Near to 18B and 18D. When petals begin to unfurl — Inside: Near to 16C and 16D with Near to 45B and 55B shading. When half-blown — Inside: At base Near to 16B Near to 45B and 55B petal edges. Reverse Side of Petals: Base Near to 16B, Rest of petals Near to 45B.

Sepals: As long as the bud (2¼ cm) — Serrated on tips with several appendages.

*Peduncle.*—3 cm in length, erect, green, Near to 152A.

Bloom:

*Size.*—5 cm in diameter, when fully expanded.

*Borne.*—Borne singly and in clusters of up to 5 blooms.

*Form.*—High centered blooms reflex gently and hold the high center.

*Petalage.*—25 to 28.

*Color.*—During first two days: Inner petals at center of flower: Near to 16B and 16D shading from near to 46A and 68B. Outer petals: Near to 16D at Base shading from near to 46A and 45A on petals. Base of petals (Point of Attachment): Near to 19A. Reverse of petals: Near to 19A and near to 46A and 68B. General Tonality from a distance: Red and yellow, near to 16D shading near to 46A and 68B with the sun.

*Color change.*—As bloom ages: The amount of red near to 46B decreases on petals. General tonality: Red and yellow blend — near to 16D and 16B and Near to 46A and 68B. After three or more days: Near to 4D, 46A and 68B.

Petals:

*Texture.*—Thick with good substance.

*Appearance.*—Velvety.

*Form.*—Oval, curling gently as bloom opens.

*Arrangement.*—Regular.

*Petaloids in center.*—Few.

*Persistence.*—Petals drop off cleanly.

*Fragrance.*—Strong, fruity.

*Lasting quality.*—Flower lasts 3 to 5 days on the bush and 2 to 3 days as a cut flower.

Reproductive Organs

Stamens, filaments and anthers:

*Arrangement.*—Regularly arranged around styles.

*Color.*—Yellow Near to 16A.

Pollen: Golden yellow.

Styles: Bunches, uneven length.

Stigmas:

*Color.*—Near to 16B.

Hips;

*Shape.*—Globular.

*Size.*—1½ cm.

*Color.*—Medium green with shades of light orange when hips are mature.

*Seeds.*—Do not protrude.

Plant

Form: Upright, Compact.

Growth: Vigorous, uniform branching.

Height attaiend: 26 to 28 inches when mature.

Foliage: Compound 5 to 7 leaflets.

*Size.*—Medium for a miniature, each leaf 3 to 4 cm in length.

*Quantity.*—Abundant.

*Color.*—New foliage: Upper side: Dark green near to 136A. Under side: Light green near to 136B. Old foliage: Upper side: Dark green near to 139A. Under side: Lighter green near to 139B.

*Shape.*—Oval, Pointed.

*Texture.*—Upper side: Thick, slick. Under side: Smooth.

Edge: Serrated.

Serration: Regular.

Leaf stem:

*Color.*—Reddish green.

*Underside.*—Reddish.

Stipules: Medium length, Slightly bearded.

Disease resistance: Blackspot; good. mildew; good. rust; good.

Wood:

*New wood.*—Red brown, Near to 176A. Bark: Smooth.

*Old wood.*—Near to 146B. Bark: Slightly rough.

Thorns:

*Quantity.*—Ordinary.

*Form.*—Flat base.

*Length.*—Medium 1 cm.

*Color when young.*—Near to 178A.

*Position.*—Irregular.

Prickles:

*Quantity.*—None.

Winter hardiness: Winter hardy with little die back.

I claim:

1. A new and distinct variety of rose plant of the Miniature Rose Class, substantially as herein shown and described, characterized particularly by an abundance of exhibition quality red and yellow blooms; unusually strong fragrance; firm thick petals, borne singly and in sprays, on a medium tall plant with semi-glossy dark green foliage; said plant being easy to propagate from cuttings; and said blooms being long lasting both on the plant and as cut flowers.

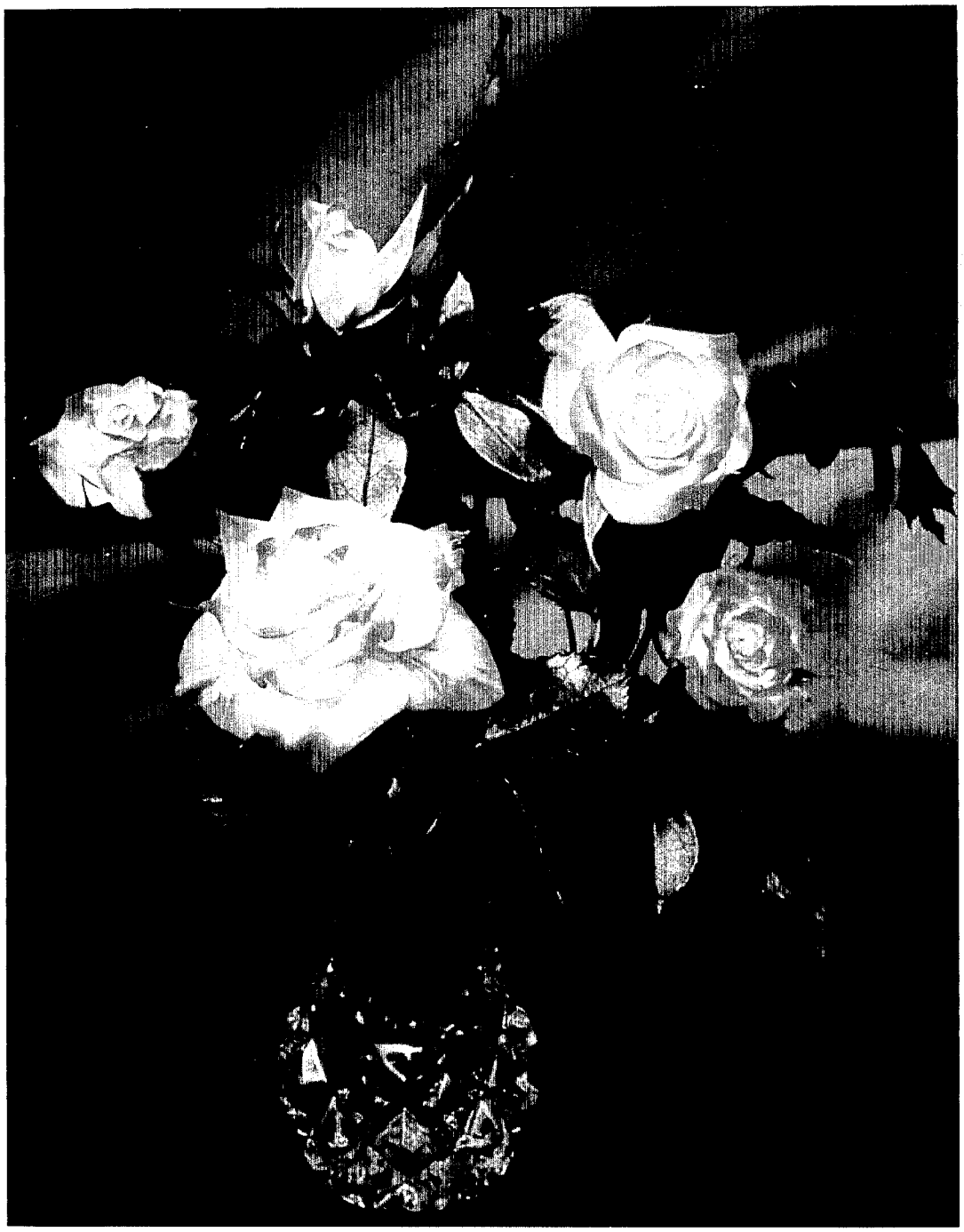

* * * * *